(12) United States Patent
Roza et al.

(10) Patent No.: US 10,392,315 B2
(45) Date of Patent: Aug. 27, 2019

(54) PROPENE PRODUCTION METHOD

(71) Applicant: Braskem S.A., Camacari-BA (BR)

(72) Inventors: Luiza Roza, Porto Alegre-RS (BR);
Luiz Claudio Macedo Cassiano Filho, Sao Vicente-SP (BR); Antonio Luiz Ribeiro de Castro Morschbacker, Campinas-SP (BR)

(73) Assignee: Braskem S.A., Camacari-BA (BR)

(*) Notice: Subject to any disclaimer, the term of this patent is extended or adjusted under 35 U.S.C. 154(b) by 0 days.

(21) Appl. No.: 15/034,367

(22) PCT Filed: Nov. 8, 2013

(86) PCT No.: PCT/BR2013/000469
§ 371 (c)(1),
(2) Date: Aug. 30, 2016

(87) PCT Pub. No.: WO2015/066778
PCT Pub. Date: May 14, 2015

(65) Prior Publication Data
US 2016/0368833 A1    Dec. 22, 2016

(51) Int. Cl.
| | | |
|---|---|---|
| C12P 5/02 | (2006.01) | |
| C07C 1/24 | (2006.01) | |
| C07C 6/04 | (2006.01) | |
| C12P 7/04 | (2006.01) | |
| C07C 5/22 | (2006.01) | |
| C12P 7/06 | (2006.01) | |
| C12P 7/16 | (2006.01) | |
| C07C 5/25 | (2006.01) | |

(52) U.S. Cl.
CPC .............. *C07C 1/24* (2013.01); *C07C 5/2213* (2013.01); *C07C 5/2506* (2013.01); *C07C 6/04* (2013.01); *C12P 5/026* (2013.01); *C12P 7/04* (2013.01); *C12P 7/065* (2013.01); *C12P 7/16* (2013.01); *C07C 2521/04* (2013.01); *C07C 2521/08* (2013.01); *C07C 2521/10* (2013.01); *C07C 2521/12* (2013.01); *C07C 2523/02* (2013.01); *C07C 2523/06* (2013.01); *C07C 2523/10* (2013.01); *C07C 2523/28* (2013.01); *C07C 2523/30* (2013.01); *C07C 2523/36* (2013.01); *C07C 2529/04* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 4,539,293 A * | 9/1985 | Bergstrom | ............... | C12P 7/16 435/160 |
| 5,753,474 A * | 5/1998 | Ramey | ..................... | C12P 7/52 435/136 |
| 6,420,619 B1 | 7/2002 | Gartside et al. | | |
| 6,683,019 B2 | 1/2004 | Gartside et al. | | |
| 8,440,874 B2 | 5/2013 | Ramachandran et al. | | |
| 2011/0305900 A1* | 12/2011 | Devisme | ............... | C08F 255/02 428/344 |

FOREIGN PATENT DOCUMENTS

| | | |
|---|---|---|
| EP | 0498573 A1 | 1/1992 |
| WO | 2004078336 A2 | 9/2004 |
| WO | 2009070858 A1 | 6/2009 |
| WO | 2010000649 A1 | 1/2010 |
| WO | 2011161045 A1 | 12/2011 |
| WO | 2013071174 A3 | 5/2013 |

OTHER PUBLICATIONS

Iwamoto et al. (J. Phys. Chem. C Letters, vol. 111, No. 1, 2007 pp. 13-15).*
Krouwel et al., Continuous isopropanol-butanol-ethanol fermentation by immobilized Clostridium beijerinckii cells in a packed bed fermenter, Enzyme Microbiology Technology, vol. 5, p. 46-54, 1983.
George et al., Acetone, Isopropanol, and Butanol Production by Clostridium beijerinckii (syn. Clostridium butylicum) and Clostridium aurantibutyricum, Applied and Environmental Microbiology, Mar. 1983, p. 1160-1163.
Krouwel et al., Continuous IBE fermentation by immobilized growing Clostridium beijerinckii cells in a stirred-tank fermentor, Biotechnology and Bioengineering, vol. XXV, p. 281-299, 1983.
Antal, Jr. et al., Mechanism and Kinetics of the Acid-Catalyzed Dehydration of 1- and 2-Propanol in Hot Compressed Liquid Water, Ind. Eng. Chem. Res. 1998, 37, p. 3820-3829.
Nel et al., Fischer-Tropsch Aqueous Phase Refining by Catalytic Alcohol Dehydration, Ind. Eng. Chem. Res., 2007, 46, p. 3558-3565.
Lee et al., Metabolic Engineering of Clostridium acetobutylicum ATCC 824 for Isopropanol-Butanol-Ethanol Fermentation, Applied and Environmental Microbiology, Mar. 2012, p. 1416-1423.
Dusseaux et al., Metabolic engineering of Clostridium acetobutylicum ATCC 824 for the high-yield production of a biofuel composed of an isopropanol/butanol/ethanol mixture, Metabolic Engineering, vol. 18, p. 1-8, 2013.

(Continued)

*Primary Examiner* — Hope A Robinson
(74) *Attorney, Agent, or Firm* — Duane Morris LLP

(57) ABSTRACT

An integrated process for the production of propene from a mixture of alcohols obtained by IBE (Isopropanol-Butanol-Ethanol) fermentation from at least one renewable source of carbon is disclosed. The process is characterized by dehydration of the alcohols in order to generate ethene, propene and linear butenes, respectively. The olefin mixture is then directed to an isomerization bed in order to generate 2-butene from 1-butene, followed by a metathesis bed to react ethene and 2-butenes to generate additional propene. This process exhibits a yield in carbon moles higher than 90% propene with respect to the alcohols produced in the fermentation step.

30 Claims, No Drawings

(56) References Cited

OTHER PUBLICATIONS

Jang et al., Metabolic engineering of Clostridium acetobutylicum for the enhanced production of isopropanol-butanol-ethanol fuel mixture, Biotechnology Progress, vol. 29, No. 4, p. 1083-1088, 2013.

* cited by examiner

PROPENE PRODUCTION METHOD

FIELD OF THE INVENTION

The present invention discloses a new process for the production of propene from a mixture of alcohols produced in IBE (Isopropanol-1-butanol-ethanol) fermentation from at least one renewable source of carbon, wherein the yield of carbon is higher than 90% propene with respect to the alcohols produced in the fermentation.

PRIOR ART DESCRIPTION

Propene is an olefin of great industrial importance, produced conventionally by petrochemical processes by refining oil and by thermal or catalytic cracking, or as a co-product of the production of ethene from natural gas. Alternatively, in scenarios with availability of low-cost propane and unavailability of propene, the dehydrogenation of propane may prove to be an economically feasible option (Propylene, Jamie G. Lacson, CEH Marketing Research Report-2004, Chemical Economics Handbook-SRI International).

Propene is employed in the production of a variety of products, such as homo- and copolymers, propylene oxide and acrylonitrile, besides being used, on a smaller scale, in the production of isopropanol and epichlorohydrin, among other chemical products.

The fact that the conventional production of propene is linked to fluctuations and limitations of the production of other products has led one to evaluate the employ of alternative pathways for the production thereof. In view of this scenario and considering other benefits associated to environmental issues, production pathways of propene from renewable sources of carbon have been studied ("Green Propylene", Nexant, January 2009).

Among the pathways based on renewable raw materials, the following are pointed out:

(i) gasification of biomass for the production of synthesis gas followed by synthesis of bio-methanol. Propene is then produced by the pathways "methanol to olefins" or "methanol to propene";

(ii) fermentation of sugars for the production of bio-ethanol followed by dehydration to ethene, a part thereof being subjected to dimerization reaction for producing a mixture of 1-butene and 2-butenes (cis- and trans-isomers). The 1-butene molecules produced are isomerized to 2-butenes, which in turn are reacted with ethene in metathesis reaction for the production of propene;

(iii) fermentation of sugars or gasification of biomass for the production of bio-butanol followed by dehydration to a mixture of 1-butene and 2-butenes (cis- and trans-isomers). After isomerization of the 1-butene to 2-butenes molecules, the 2-butenes molecules formed are reacted with ethene, obtained by dehydrating bio-ethanol, via metathesis reaction for the production of propene as described in (ii).

In pathway (iii) the ethene and butene olefins are obtained from the dehydration of the respective alcohols. Such pathway presents itself as an opportunity for fermentations known as ABE (Acetone-1-Butanol-Ethanol) and IBE (Isopropanol-1-Butanol-Ethanol) which produce the alcohols of interest in the same fermentative medium. The IBE fermentation has the advantage of generating isopropanol, from which propene can be directly obtained by dehydration.

The microorganisms employed in the ABE fermentations are bacteria of genus *Clostridium*. Such bacteria are spore forming ones, strictly anaerobic and capable of fermenting pentoses and hexoses. The metabolic pathways that are typical of this genus are: acidogenic pathway, by which sugars are fermented, generating acetic, butyric and lactic acids, besides hydrogen and carbon dioxide, and the solvatogenic pathway, wherein the co-fermentation of sugars and of part of the acids formed occurs generating acetone, 1-butanol, and ethanol. Some species of *Clostridium*, either wild or genetically modified, may exhibit an extra pathway in which acetone is hydrogenated to isopropanol, resulting in IBE fermentation.

In the 1980s, in a search for alternatives to the use of petrochemical raw materials for the production of isopropanol and butanol, a few studies on IBE fermentations stood out, such as "Acetone, Isopropanol, and Butanol Production by *Clostridium beijerinckii* (syn. *Clostridium butylicum*) and *Clostridium aurantibutyricum*" (Applied and Environmental Microbiology, vol. 45, n. 3, p. 1160-1163), which exhibits scanning on different species of anaerobic bacteria known for the ABE production, identifying five isopropanol producing species.

Other two papers published by Krouwel et al., "Continuous IBE Fermentation by Immobilized Growing *Clostridium beijerinckii* Cell in a Stirred-Tank Fermentor" (Biotechnology and Bioengineering, vol. 25, p. 281-299, 1983) and "Continuous Isopropanol-Butanol-Ethanol fermentation by immobilized *Clostridium beijerinckii* cells in a packed bed fermenter (Enzyme Microbiology Technology, vol. 5, p. 46-54, 1983) present strategies of continuous fermentation using the bacterium *Clostridium beijerinckii*, supported on a calcium alginate bed. The papers show promising results for use of biocatalyzing particles repeatedly in successive fermentations.

From 2012, studies involving the co-production of 1-butanol by fermentation, chiefly aiming at its application as bio-fuel, have brought new perspectives for co-production of isopropanol, 1-butanol and ethanol. In "Metabolic Engineering of *Clostridium acetobutylicum* ATCC 824 for Isopropanol-Butanol-Ethanol Fermentation" (Applied and Environmental Microbiology, vol. 78, n. 5. p. 1416-1423, 2012), a genetic modification of an ABE producing bacterium for the conversion of acetone to isopropanol was reported. The use of the genetically modified bacterium in a fermentation process in fed batch, combined with the in situ removal of the solvents lead to yield values, final concentration and productivity of the mixture of alcohols (isopropanol, 1-butanol and ethanol) of 0.30 g/g in glucose, 20.4 g/l and 0.45 g/l·h, respectively. Such a performance, according to the authors, was superior to those achieved by using IBE naturally producing microorganisms.

In "Simultaneous production of isopropanol, butanol, ethanol and 2,3-butanediol by *Clostridium acetobutylicum* ATCC 824 engineered strains" (AMB Express, vol. 2, n. 45, 2012), one reported genetic alterations that lead to conversions of acetone to isopropanol higher than 95% by mass, besides the co-production of 2,3-butanediol. On the other hand, the article "Introducing a single secondary alcohol dehydrogenase into butanol-tolerant *Clostridium acetobutylicum* Rh8 switches ABE fermentation to high level IBE fermentation" (Biotechnology for Biofuels, vol. 5, n. 44, 2012), presented high conversion to IBE (0.31 g/g in glucose) with total conversion of acetone to isopropanol. More recently, in "Metabolic engineering of *Clostridium acetobutylicum* ATCC 824 for the high-yield production of a biofuel composed of an isopropanol/butanol/ethanol mixture" (Metabolic Engineering, vol. 18, p. 1-8, 2013) one reported a record mark of yield values, final concentration of IBE and productivity (0.34 g/g in glucose, 21 g/l and 0.7 g/·h, respectively).

In "Metabolic Engineering of *Clostridium acetobutylicum* for the Enhanced Production of Isopropanol-Butanol-Ethanol Fuel Mixture" (American Institute of Chemical Engineers Journal, vol. 29, n. 4, p. 1083-1088, 2013), one described the IBE fermentation on a bench and pilot scale. On a pilot scale, one achieved high values for the final concentration of IBE (28.5 g/l), yield (0.37 g/g in glucose) and productivity (0.5 g/l·h), but with a weight ratio of isopropanol:1-butanol:ethanol of 1:4:3, unlike the weight ratios usually reported (about 5:15:1).

A problem associated to the IBE and ABE fermentations is the high cost of separation of the products. The processes of recovering the alcohols from the ABE or IBE fermentative wort reported in the literature, in general, have the objective of obtaining them in isolation, especially 1-butanol.

In WO2010000649, one described the use of the ABE fermentation with a view to obtain 1-butanol, using species of *Clostridium*. The conversion of substrates to acetone, 1-butanol and ethanol and the subsequent recovery of 1-butanol by distillation were reported. The possibility of employing alternative methods for separating the product of interest, like membrane and gas trailing separation was also cited.

The detailed description of the application of membranes for separation via pervaporation of one or more organic components of an aqueous solution, among these that of a fermented ABE wort, can be found in document WO2013071174.

The dehydration of alcohols to the corresponding olefins is already quite known. In document WO2004078336, for instance, one reported the dehydration of alcohols in γ-alumina catalysts with high values of conversion to the corresponding olefins. WO2011161045 presents dehydration of alcohols with at least two carbon atoms using zeolites, modified zeolites, alumina, silica-alumina, silico-aluminophosphates and alumina modified with Si, Ti, Zr or F.

The simultaneous dehydration of alcohols was described for the first time in document WO2009070858, which reports the joint dehydration of ethanol and 1-butanol, obtained in different fermentations, in a single reactor for obtaining ethene and a mixture of butenes.

The production of propene by the isopropanol dehydration process was described in document EP0498753, in which the examples presented selectivity higher than 90% in high conversions. Other references for dehydration of isopropanol can be found in "Mechanism and Kinetics of the Acid-Catalyzed Dehydration of 1- and iso-propanol in Hot Compressed Liquid Water" (Antal, M et al, Ind. Eng. Chem. Res. 1998, 37, 3820-3829) and in "Fisher-Tropsch Aqueous Phase Refining by Catalytic Alcohol Dehydration" (Nel, R. et al., Ind. Eng. Chem. Res. 2007, 46, 3558-3565).

The process of producing propene by metathesis reaction of the olefins ethene and 2-butenes is quite well described in the literature. U.S. Pat. Nos. 6,420,619, 6,683,019 and 8,440,874 report the catalysts traditionally used, as for instance, inorganic oxides containing a metal or metallic oxides supported on silica or alumina. The reaction involved in the metathesis process between ethene and 2-butenes molecules is represented in reaction (01):

  (01)

1-Butene molecules do not react with ethene, but they can participate in the reactions (02) and (03). Thus, with a view to maximizing propene, 1-butene should be isomerized to 2-butenes, before the metathesis reaction between ethene and 2-butenes.

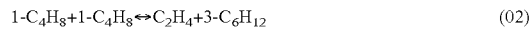  (02)

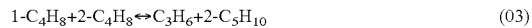  (03)

Another isomer that should be avoided when one wishes maximum production of propene from the metathesis reactions between ethene and butenes is isobutene, which reacts with 2-butenes according to reaction (04):

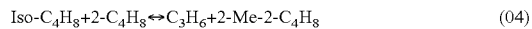  (04)

In order to minimize the parallel reactions between and, as a result, maximize the production of propene, the metathesis reaction is, in general, operated with excess ethene.

Document US2011305900 proposes dehydration of alcohols obtained from IBE fermentation for the production of propene. However, unlike the present invention US2011305900 does not teach one to obtain the mixture of olefines ethene, propene and linear butenes from the dehydration of the mixture of the respective alcohols. In an embodiment, isopropanol is separated from the other fermentation products, before being led to the step of dehydration to propene. In an alternative embodiment, ethanol and 1-butanol generated in the fermentation are separated from the other alcohols before being led to the dehydration step. Besides, the process presented in US2011305900 applied to microorganism of the genus *Clostridium* known from the art would result in a low utilization of carbon from the alcohols in propene due to the non-optimized ratio of ethanol:1-butanol, unlike the process proposed in the present invention, which teaches one to achieve maximum utilization of carbon from the alcohols produced in the IBE fermentation for conversion to propene, regardless of the ratio ethanol:1-butanol from the fermentation.

Despite the large number of publications related to the dehydration of alcohols to olefins, there is no report in the literature of the co-dehydration of a mixture of isopropanol, 1-butanol and ethanol for obtaining a mixture of the corresponding olefins with high conversions and high selectivities to ethene, propene and linear butenes.

Objectives of the Invention

In view of the foregoing, it is an objective of the invention to provide a process for the production of propene from a mixture of alcohols produced in an IBE fermentation of at least one renewable source of carbon.

It is another objective of the invention to provide an integrated process with carbon yield higher than 90% propene with respect to the alcohols produced in an IBE fermentation.

BRIEF DESCRIPTION OF THE INVENTION

The objectives of the present invention are achieved by the following steps:
a) Fermenting a renewable source of carbon for the production of a mixture of alcohols comprising ethanol, isopropanol and 1-butanol;
b) Simplified removal of the alcohols from the fermentative wort to generate an aqueous solution containing chiefly ethanol, isopropanol and 1-butanol;
c) Joint dehydration of the alcohols to produce a mixture of olefins comprising chiefly ethene, propene and linear butenes, the linear butenes being a mixture of 1-butene and 2-butenes (cis- and trans-isomers), besides water and by-products, among which oxygenated compounds;

d) Removal of water, oxygenated compounds and other by-products from the mixture of olefins, to generate a mixture of olefin comprising chiefly ethene, propene and linear butenes; and e) passing the mixture of olefins through an isomerization bed so that 1-butene is isomerized to 2-butene and subsequently passing the mixture of olefins comprising chiefly ethene, propene and 2-butenes through a metathesis bed, for reaction between ethene and 2-butenes, generating additional propene.

The mole ratio ethene:linear butenes being corrected to be between 1:1 and 1.3:1, by means of one of the alternatives from the group formed by:

(i) Addition of a stream containing ethanol to the process of step (c);

(ii) Addition of a stream of ethene to the process of step (e);

(iii) Addition of a stream containing ethanol to the process of step (c) and of a stream containing ethene in step (e)

DETAILED DESCRIPTION OF THE INVENTION

The present invention presents a new process for the production of propene from a mixture of alcohols (isopropanol, 1-butanol and ethanol), obtained by IBE fermentation. The alcohols are co-dehydrated to their corresponding olefins and the mixture of olefins generated is sent to a isomerization/metathesis system. In order to obtain the proportion of ethene and 2-butenes that favors the metathesis with maximization of the production of propene and so that the conversion to propene of the alcohols produced in the fermentation will be higher than 90% in carbon mole, one of the following procedures should be adopted:

i) Addition of a stream containing ethanol to the process in the dehydration step, so that the molar ratio of ethanol:1-butanol will be between 1:1 and 1.3:1, as a result the molar ratio of ethene:butenes at the outlet of the dehydration reactor will be between 1:1 and 1.3:1; or ii) Addition of a stream containing ethene to the stream coming out of the co-dehydration reactor, so that the molar ratio of ethene:butenes of the stream to be sent to the isomerization/metathesis system will be between 1:1 and 1.3:1;

iii) Addition of a stream containing ethanol to the co-dehydration step and a stream containing ethene to the stream coming out of the co-dehydration reactor, so that the molar ratio of ethene:butenes of the stream to be set to the isomerization/metathesis system will be between 1:1 e 1.3:1.

In the procedure (iii), the adjustment of the ratio ethene:butenes of the stream to be sent to the isomerization/metathesis system is made in two step. A part of the adjustment necessary to adjust the molar ratio ethene:butenes is obtained by adding a certain amount of ethanol to the stream to be sent to the dehydration reactor and the remaining ethene necessary to the adjustment of the molar ratio ethene:butenes to between 1:1 and 1.3:1 is added directly to the stream to be sent to the isomerization and metathesis system.

In a first embodiment, the process for producing propene of renewable origin from a mixture of alcohols obtained by IBE fermentation disclosed in the present invention comprises the following steps:

a) Fermentation of a renewable source of carbon for the production of a mixture of alcohols comprising ethanol, isopropanol and 1-butanol;

b) Simplified removal of the alcohols from the fermentative wort to generate an aqueous solution containing chiefly ethanol, isopropanol and 1-butanol;

c) Addition of ethanol to the alcohols formed, so that the final aqueous solution will have molar ratio ethanol:1-butanol between 1:1 and 1.3:1;

d) Joint dehydration of the alcohols in specific conditions for producing a mixture of olefins containing chiefly ethene, propene and linear butenes, the linear butenes being formed by a mixture of 1-butene and 2-butenes (cis- and trans-isomers), in addition to water and other by-products, among which oxygenated compounds;

e) Removal of water, oxygenated compounds and other by-products, to generate a mixture of olefins comprising chiefly ethene, propene and linear butenes;

f) Passage of the mixture of olefins through an isomerization bed so that 1-butene will be isomerized to 2-butenes and subsequently passage of the mixture of olefins comprising chiefly ethene, propene and 2-butenes through a metathesis bed, for reaction between ethene and 2-butenes, generating additional propene.

In a second embodiment, the production of propene of renewable origin passes through following steps:

a) Fermentation of a renewable source of carbon for the production of a mixture of alcohols containing ethanol, isopropanol and 1-butanol;

b) Simplified removal of the alcohols from the fermentative wort to generate an aqueous solution containing chiefly ethanol, isopropanol and 1-butanol;

c) Joint dehydration of the alcohols in specific conditions to produce a mixture of olefins containing chiefly ethene, propene and linear butenes, the linear butenes being formed by a mixture of 1-butene and 2-butenes (ci- and trans-isomers), in addition to water and other by-products, among which oxygenated compounds;

d) Removal of water, oxygenated compounds and other by-products, to generate a mixture of olefins containing chiefly ethene, propene and linear butenes;

e) Addition of ethene to this mixture of olefins, so that the final mixture will have molar ratio ethene:linear butenes between 1:1 and 1.3:1;

f) Passage of the mixture of olefins through an isomerization bed so that 1-butene will be isomerized to 2-butenes and subsequently passage of the mixture of olefins comprising chiefly ethene, propene and 2-butenes through a metathesis bed, for reaction between ethene and 2-butenes, generating additional propene.

In a third embodiment, the production of propene of renewable origin passes through the following steps:

a) Fermentation of a renewable source of carbon for the production of a mixture of alcohols comprising ethanol, isopropanol and 1-butanol;

b) Simplified removal of the alcohols from the fermentative wort to generate an aqueous solution containing chiefly ethanol, isopropanol and 1-butanol;

c) Addition of stream containing ethanol to the alcohols formed, so that the final aqueous solution will have molar ratio ethanol:1-butanol equal to or lower than 1:1;
d) Joint dehydration of the alcohols in specific conditions for producing a mixture of olefins containing chiefly ethene, propene and linear butenes, the linear butenes being formed by a mixture of 1-butene and 2-butenes (cis- and trans-isomers), in addition to contaminants, among which oxygenated compounds;
e) Removal of water, oxygenated compounds and other contaminants from the stream formed in (d), to generate a mixture of olefins comprising ethene, propene and linear butenes;
f) Addition of a certain amount of ethene to this mixture of olefins, so that the final mixture will have molar ratio ethene:linear butenes between 1:1 and 1.3:1;
g) Passage of the mixture of olefins through an isomerization bed, so that 1-butene will be isomerized to 2-butenes and subsequently passage of the mixture of olefins comprising chiefly ethene, propene and 2-butenes through a metathesis bed, for reaction between ethene and 2-butenes, generating additional propene.

Each of the steps will be described in detail hereinafter.

Fermentation of a Source of Carbon for the Production of a Mixture of Alcohols Ethanol, Isopropanol and 1-Butanol Throughout the text, one understands by renewable source of carbon any biomass that is fermentable by microorganisms of the genus *Clostridium*. Among renewable sources applicable to the present invention are sugars in solution that come from, for example, but not limited to, sugar-cane or sugar-beet; starch hydrolysates obtained, for instance, from, but not limited to, maize and cassava; hydrolysates from lignocellulosic materials obtained from, but not limited to, straw, bagasse and wood. Alternatively, one may use sources of carbon derived from different raw materials.

The fermentation step of the process of the present invention is carried out by using microorganisms of the genus *Clostridium*, for example, but not limited to, *Clostridium beijerinckii, Clostridium acetobutylicum, Clostridium butylicum, Clostridium aurantibutyricum, Clostridium tyrobutyricum* and *Clostridium saccarabutylicum*. The organisms used may be either wild or genetically modified.

The fermentation process may be carried out according to the methods described in the literature, as for example, but not limited to the processes presented in U.S. Pat. No. 5,753,474 and in "Production of butyric acid and butanol from biomass" (Final Report for U.S. Department of Energy, 2004).

The microorganisms may be used in conventional fermentation method in two steps. In the first step, the acidogenic phase takes place, when the main products are organic acids (for example, acetic and butyric acid). This phase is also characterized by the microorganism's growth. In the second step, the solvatogenic one, the microorganism begins to produce solvents and alcohols like acetone, isopropanol, 1-butanol and ethanol.

The acidogenic and solvatogenic steps may take place on the same reactor or on different reactors. The fermentation process may be operated in a continuous manner, in batches or in batches fed with the microorganisms, either immobilized or not.

Residues of the fermentation process, such as organic acids, oxygenated compounds, nitrogenated compounds and unfermented sugars, may be converted, through processes like biodigestion, into fuels, which may be used in the same process for generating energy. The fuels generated may be used, for instance, but not limited to ovens used in the alcohol dehydration step.

The cellular biomass generated may be separated and employed for protein-enrichment of animal feed or the source of nitrogen in agricultural fertilizers.

Simplified Removal of the Alcohols from the Fermented Wort to Generate an Aqueous Solution Containing Chiefly Isopropanol, 1-Butanol and Ethanol By simplified removal one understands the separation of the mixture of alcohols, still with a certain amount of water, from the rest of the composition of the fermented medium. Such an operation differs from the conventional separation, because it does not aim at the individual separation of each of the alcohols formed, but simply the removal from the wort.

The fermented wort is, therefore, subjected to a step of separating the mixture of alcohols from the rest of the wort composition through conventional processes of separating solids for removal of the cellular material generating a raw aqueous stream containing the alcohols formed in the fermentation.

The raw aqueous stream containing the alcohols may further contain contaminants like organic acids and salts. The removal of these contaminants may be carried out by conventional methods known in the area. In an embodiment, the aqueous mixture is subjected to neutralization and the removal of the salts, including organic acids, formed in the neutralization. The removal of the salts may be carried out by usual techniques, such as, for example, but not limited to the passage of the mixture through ion-exchange resins.

After removal of the salts, the aqueous stream containing the mixture of alcohols may be subjected to an operation for reduction of the water contents. The operation may be carried out by conventional method of the area, as for example, but not limited to distillation. The water content at the end of the operation is preferably lower than 50% by mass.

The process of the present invention may be characterized in that the dehydration and isomerization/metathesis steps are physically in different places from that of the fermentation step, and need transportation of the intermediate product. In this case, it may be advantageous to remove a smaller amount of water, so that the transportation between the units will have a lower cost.

Addition of a Stream Containing Ethanol to the Alcohols Formed

In the first embodiment, in which the molar ratio ethanol:1-butanol is corrected to be between 1:1 and 1.3:1, the necessary amount of ethanol for correction is added to the final solution containing the alcohols generated in the fermentation medium. The molar ratio ethanol:1-butanol should be corrected to be between 1:1 and 1.3:1, and preferably there should be an excess ethanol with respect to butanol.

In the third embodiment, in which the molar ratio ethene:butenes is corrected by adding a stream containing ethanol to the final solution containing the alcohols generated in the fermentation medium and by adding a stream containing ethene to the stream of olefins to be sent to the isomerization and metathesis steps, so that the molar ratio ethene:butenes in the stream to be sent to the isomerization and metathesis steps will be between 1:1 and 1.3:1.

The stream containing ethanol added to the final solution containing the alcohols produced in the fermentation may come from a conventional alcoholic fermentation process by yeast.

In a form of the invention, the stream containing added ethanol comprises hydrated or anhydrous ethanol, from an external distillery. Preferably, one adds a stream of fuel grade hydrated ethanol.

In another form of the invention, the stream of ethanol added to the mixture of alcohols comes from the fermentation process linked to the IBE fermentation unit.

Joint Dehydration of the Alcohols

The final aqueous solution containing the alcohols produced in the fermentation, possibly with addition of a stream containing ethanol, is vaporized and led in gas phase to a co-dehydration reactional system for the formation chiefly of the olefins ethene, propene and linear butenes. The step of joint dehydration of the alcohols of the present invention takes place at a temperature ranging from 250° C. to 600° C., preferably from 300° C. to 500° C. The pressure in the dehydration step should be in the range from 100 to 2000 kPa (1 to 20 bar), preferably from 100 to 1500 kPa (1 to 15 bar).

Since the reactions of dehydration of ethanol, isopropanol and 1-butanol to the respective olefins are endothermal, the process may be conducted either in the isothermal mode or in the adiabatic mode. The dehydration reactor may contain a fixed bed or a fluidized bed. Preferably, the process is conducted in the adiabatic mode with fixed bed.

In adiabatic system, one may, optionally, add an amount of vapor or water or another inert material and with high specific heat, so as to reduce the drop in temperature in the reactor. In the present invention, the inert material employed is preferably water. In this case, the total weight concentration of water at the inlet of the reactor may range from 5 to 80%, preferably from 25 to 70%, and more preferably from 45 to 65%. The total weight concentration of water at the inlet of the reactor includes the water remaining from the simplified purification process of the mixture of alcohols.

In the process of the present invention, one may use only one reactor or an array of reactors in series and in parallel, so that the effluent from the first rector, composed chiefly by water and olefins (ethene, propene and butenes), serves as inert for the next reactors that receive a fresh load of the aqueous stream containing the alcohols.

In the operations modes in which one uses more than one reactor in the co-dehydration step, all of them may be operated in the same range of temperature from 250° C. to 500° C., preferably from 300° C. to 450° C., but not necessarily at the same temperature. In an alternative mode of operation, the last reactor may be operated in a range of temperature higher than the others, namely from 300° C. to 600° C., more preferably from 350° C. to 500° C. In this latter case, the objective in raising the temperature is to minimize the content of ethers obtained by intermolecular dehydration of the alcohols, mainly ethylic ether, the separation of which from the olefins butenes in the purification step is difficult. Ethylic ether, upon being subjected to higher temperatures, undergoes intermolecular dehydration, generating two ethene molecules per ethylic ether molecule.

The catalysts for the dehydration reaction may be chosen from the acidic catalysts known from the prior art, as being efficient for dehydration of aliphatic alcohols to the corresponding olefins. Examples of catalysts suitable for the reactions of dehydration of ethanol to ethene, isopropanol to propene and 1-butanol to butenes, include, but not limited to catalysts based γ-alumina; silica-alumina; metallic oxides like, for example, titanium, hafnium, zirconium and tungsten; zeolites as well as combination thereof. Preferably, one employs catalysts based on γ-alumina, silica-alumina, zeolites and mixtures thereof. Preferably, the catalyst should exhibit large surface area and may, optionally, be modified with phosphorus and/or metals like, but not limited to Mg, Ca, La, Ni, Ce, Zn, Co, Ag, Fe, Cu or a mixture of two or more thereof.

The co-dehydration step presents high convention of the alcohols and high selectivity to olefins, so that the molar yield is higher than 95%, preferably higher than 97%. The dehydration technology is considered a clean technology, because it generates water as by-product, which in turn may be reused in the process, for instance, in the fermentation step.

Unlike the dehydration of ethanol and isopropanol, the dehydration of alcohols with 4 or more carbon atoms is not selective, a range of isomer products being generated. From the dehydration of 1-butanol, one can generate 1-butene, cis-2-butene, trans-2-butene and isobutene. Other by-products usually formed, in smaller quantity, are oxygenated products such as dibutylether, butylaldehyde, carbon monoxide and carbon dioxide, besides other hydrocarbons.

The dehydration conditions may be adjusted in order to minimize the formation of isobutene, reduce the formation of 1-butene and maximize the formation of 2-butenes during the dehydration of 1-butanol. Within the temperature ranges specified above, the optimum condition for simultaneous dehydration of alcohols with conversion of carbon higher than 97% for olefins and selectivity in carbon higher than 60% for dehydration of 1-butanol to 2-butenes takes place in residence times ranging from 10 to 240 seconds, preferably from 60 to 150 seconds. In these conditions, the contents of isobutene formed in the reaction of dehydration of 1-butanol is lower than 0.5% molar and the other by-products (dibutylic ether, butyric acid, carbon monoxide and carbon dioxide) are found in amounts smaller than 100 ppm. The selectivity of the dehydration of 1-butanol to 2-butenes is higher than 60%, summing up the cis- and trans-isomers.

The main impurities present in the stream of olefins at the outlet of the reactor are ethers (diethyl ether, di-isopropyl ether and dibutyl ether), isobutene, ethane, propane, butane, CO, CO2, acetaldehyde, CH4, H2, in addition to the unreacted alcohols and occasionally acetone.

Purification of the Products from the Dehydration Reactions for Generation of a Mixture of Olefins Isomerization catalysts and metathesis catalysts are known for exhibiting high sensitivity to poisons, which include water, carbon dioxide, oxygenated, sulfured, and nitrogenated compounds, in addition to heavy metals. In this way, with a view to guarantee longer life of the isomerization and metathesis catalysts, the stream of olefins obtained by co-dehydration of alcohols to their respective olefins, according to the present invention, shall be subjected to purification processes for removal of water and other by-products, as well as decomposition products thereof, in addition to any other contaminant resulting from the fermentation process that may still be present in the stream.

The purification steps employed are known in the area. The steps described hereinafter compose only an embodiment, without limiting the process. Other embodiments based on purification techniques known in the area may be used. In one embodiment, the outlet stream of the co-dehydration is led to a simple process for removal of water, for example, by condensation. The stream with reduced contents of water is subjected to a step of removal of carbon dioxide, as for example, passage through an alkaline wash column and, later, the stream of olefins is subjected to a compression step followed by drying. The drying by be carried out by any method known in the area, as for example, but not limited to passage through a bed of molecular sieve, zeolites, silica or other materials capable of reducing the water contents to values equal to or lower than 50 ppm, preferably equal to or lower than 30 ppm and more preferably equal to or lower than 10 ppm. The stream of olefins then follows to a cryogenic distillation process with three withdrawals of product: at the top containing the non-condensable light contaminants, at the base containing the heavy contaminants including ethers, and in the middle containing chiefly the mixture of olefins (ethene, propene and butenes), the latter being sent to the isomerization and metathesis reactions. The stream formed chiefly by ethene, propene and linear butenes may exhibit content of the respective paraffins lower than 1000 ppm.

Among the by-products generated in the co-dehydration of the alcohols, the diethyl ether has a difficulty, namely: its separation from the butenes. It is known that the formation of ethers in dehydration reactions of alcohols may be adjusted by the reaction conditions, especially temperature. In this way, the reaction conditions may be adjusted to maximize the dehydration of the diethyl ether to ethene during the co-dehydration, as described before, reducing costs in the distillation step.

Addition of a Stream Containing Ethene to the Mixture of Olefins

In the second embodiment, in which the molar ratio of ethene:linear butenes is corrected to be between 1:1 and 1.3:1 by direct addition of ethene to the mixture of olefins obtained from the dehydration of the mixture of alcohols, before the isomerization and metathesis steps, the stream containing ethene in an amount necessary for correction is added after purification of the stream. For this purpose, the degree of purity of the streams shall be compatible.

In the third embodiment, as described before, the molar ratio of ethene:linear butenes is corrected to be between 1:1 and 1.3:1 by adding a stream containing a certain amount of ethanol to the joint dehydration step and by adding a stream containing a certain amount of ethene after purification of the stream of olefins before the isomerization and metathesis steps.

The ethene added may be of renewable or petrochemical origin, or still a composition formed by a mixture thereof.

Isomerization and Metathesis of the Olefins Formed for Maximization of the Yield to Propene In the process of the invention, a stream is generated which contains chiefly olefins, propene, ethene and linear butenes (mixture of 1 and 2-butenes), the latter in the molar ratio of 1:1 and 1.3:1, besides propene (product of interest of the described process).

The dehydration conditions may be adjusted so as to maximize the formation of 2-butenes. In order to convert remaining 1-butene to 2-butenes (mixture of the cis and trans species), one may use a bed with isomerization catalyst before the metathesis reaction. The isomerization catalyst may be chosen from those known in the art, such as supported phosphoric acid, bauxite, supported alkaline metals, cobalt, iron or manganese oxides supported on alumina. Preferably, the catalyst is chosen from zinc oxide, magnesium oxide, calcium oxide, cerium oxide, thorium oxide, titanium oxide and the like, or a mixture of two or more thereof. More preferably, the catalyst used is magnesium oxide.

The isomerization catalyst, besides acting on the conversion of 1-butene to 2-butenes, acts also as a reserve bed for the metathesis catalyst, adsorbing residual poisons and, as a result, prolonging its life.

The catalyst used for the metathesis reaction may be a catalyst known from the state of the art, such as inorganic oxides containing a transition metal or supported transition metal oxides. Transition metal or transition metal oxides that may be applied in the present invention include, but are not limited to tungsten, rhenium, molybdenum, their respective oxides and mixtures thereof. The supports may be alumina, silica, silica-alumina, magnesium oxide-titanium oxide, thorium oxide, aluminum phosphate, zirconium phosphate, titanium phosphate, calcium phosphate, magnesium phosphate and the like, or a mixture of two or more thereof. Preferably, one uses alumina or silica as support. In a preferred embodiment of the invention, one employs tungsten oxide supported on silica or rhenium oxide supported on aluminum.

In another aspect of the invention, one may use isomerization-metathesis bi-functional catalysts, as for example, but not limited to the catalyst presented in U.S. Pat. No. 8,440,874.

The reaction conditions of the isomerization and metathesis steps include temperatures ranging between 50° C. and 600° C., preferably between 150° C. and 400° C., and pressures from 100 to 2000 kPa (1 and 20 bar), preferably from 100 to 1000 kPa (1 to 10 bar).

The stream of products generated in the isomerization and metathesis steps is composed chiefly by propene, ethene and non-reacted 2-butenes, in addition to other components with 5 or more carbon atoms formed in side reactions. The recovery of propene and ethene and unreacted butenes is carried out by using operations that are usual in the art. Ethene and unreacted butenes are recycled for the isomerization and metathesis steps, so that the global selectivity to propene with respect to the olefins for metathesis reaction will be higher than 90% by carbon mole, preferably higher than 92% and still more preferably higher than 94%.

Depending on the degree of purity required by the application, the propene produced according to the present invention may be subjected to additional purifying steps.

In view of the foregoing, the process of the present invention is suitable for the production with high yield of olefin propene from renewable raw material. The thus obtained propene may contain from 75 to 100% carbon of renewal origin, contents that may be certified by the rule ASTM D-6866.

The propene obtained may be employed in various applications, including for the production of polypropylene (homopolymers and copolymers), besides other totally or partially renewable products.

What is claimed is:

1. A process for producing propene from a mixture of alcohols obtained from at least one renewable source of carbon, comprising the following steps:
   a) Fermentation of at least one renewable source of carbon using a microorganism of the genus *Clostridium* for the production of a mixture of alcohols comprising ethanol, isopropanol and 1-butanol;
   b) Separation of the alcohols from a fermentative wort to generate an aqueous solution containing ethanol, isopropanol and 1-butanol;
   c) Dehydration of the alcohols to produce a mixture of olefins comprising ethene, propene and linear butenes, wherein the linear butenes comprise a mixture of 1-butene and 2-butenes (cis and trans isomers), water and by-products, comprising oxygenated compounds;
d) Removal of the water and by-products to generate a mixture of olefins comprising ethene, propene and linear butenes; and
e) Passing the mixture of olefins through an isomerization bed so that 1-butene is isomerized to 2-butenes and, subsequently, passing the mixture of olefins comprising ethene, propene and 2-butene through a metathesis bed, for a reaction between ethene and 2-butenes, to generate additional propene, wherein a molar ratio of ethene: linear butenes is corrected to be between 1:1 and 1.3:1; by means of one of the alternatives selected from the group consisting of:
(i) Addition of a stream containing ethanol to the process in step (c);
(ii) Addition of a stream containing ethene to the process in step (e); and
(iii) Addition of a stream containing ethanol to the process in step (c) and a stream containing ethene in step (e); wherein the process exhibits a yield in carbon moles higher than 90% propene with respect to the alcohols produced in step (a), wherein the microorganism is selected from the group consisting of *Clostridium beijerinckii*, *Clostridium acetobutylicum*, *Clostridium butylicum*, *Clostridium aurantibutyricum*, *Clostridium tyrobutyricum* and *Clostridium saccarobutylicum*; and wherein the propene produced exhibits 75 to 100% by mole of carbon of renewable origin.

2. The process of claim 1, wherein the microorganism is either wild-type or genetically modified.

3. The process of claim 1, wherein the ethanol added in step (c) comes from an alcoholic fermentation process by yeast.

4. The process of claim 3, wherein the ethanol added in step (c) comes from distilleries.

5. The process of claim 4, wherein the ethanol added in step (c) is fuel grade hydrated ethanol.

6. The process of claim 3, wherein the ethanol added in step (c) comes from a fermentation process linked to an isopropanol-1-butanol-ethanol (IBE) fermentation unit.

7. The process of claim 1, wherein the dehydration step (c) is conducted at temperatures ranging between 250° C. and 600° C.

8. The process of claim 7, wherein the dehydration step (c) is conducted at temperatures ranging between 300° C. and 500° C.

9. The process of claim 1, wherein the dehydration step (c) is conducted under pressure of between 100 and 2000 kPa (1 and 20 bar).

10. The process of claim 9, wherein the dehydration step (c) is conducted under pressure of between 100 and 1500 kPa (1 and 15 bar).

11. The process of claim 1, wherein the process is conducted in an adiabatic mode.

12. The process of claim 11, wherein the mixture of alcohols is fed to a dehydration reactor in the presence of 5% to 80% by mass of water.

13. The process of claim 12, wherein the mixture of alcohols is fed to the dehydration reactor in the presence of 25% to 70% by mass of water.

14. The process of claim 13, wherein the mixture of alcohols is fed to the dehydration reactor in the presence of 45% to 65% by mass of water.

15. The process of claim 1, wherein the dehydration step (c) is conducted in an array of reactors in series and in parallel.

16. The process of claim 15, wherein the array of reactors are operated in a temperature of between 250° C. and 500° C.

17. The process of claim 16, wherein the array of reactors are operated in a temperature of between 300° C. and 450° C.

18. The process of claim 15, wherein the array of reactors has one reactor that is operated between 300° C. and 600° C.

19. The process of claim 18, wherein the array of reactors has one reactor that is operated between 350° C. and 500° C.

20. The process of claim 11, wherein the array of reactors operate at a resident time between 10 and 240 seconds.

21. The process of claim 20, wherein the array of reactors operate at a resident time between 60 and 150 seconds.

22. The process of claim 1, wherein the dehydration step (c) exhibits molar yield of the olefins propene, linear butenes and ethanol higher than 95%.

23. The process of claim 22, wherein the dehydration step (c) exhibits molar yield of the olefins propene, linear butenes and ethanol higher than 97%.

24. The process of claim 1, wherein the dehydration reaction of 1-butanol exhibits molar selectivity for isomers of 2-butene higher than 60%.

25. The process of claim 1, wherein the isobutene contents in the outlet stream of the dehydration step is lower than 0.5% by mole.

26. The process of claim 1, wherein at the outlet of the dehydration step (c) the stream purification of consisting of condensation, alkaline washing, drying and cryogenic distillation takes place.

27. The process of claim 26, wherein the drying is carried out by passing the stream through a molecular sieve.

28. The process of claim 1, wherein the water contents in the purified mixture of olefins after the purification step (d) are equal to or lower than 50 ppm.

29. The process of claim 28, wherein the water contents in the purified mixture of olefins after the purification step (d) are equal to or lower than 10 ppm.

30. The process of claim 1, wherein the stream containing ethene added to the purified mixture of olefins contains ethene of renewable origin, ethene of petrochemical origin or a mixture thereof.

* * * * *